United States Patent
Lamprich et al.

(10) Patent No.: US 7,096,870 B2
(45) Date of Patent: Aug. 29, 2006

(54) DISPOSABLE STERILE SURGICAL DRAPE AND ATTACHED INSTRUMENTS

(76) Inventors: Lonnie Jay Lamprich, 1312 Glenwood Ave., Oklahoma City, OK (US) 73116; Bradley Keith Lamprich, 1312 Glenwood Ave., Oklahoma City, OK (US) 73116

( * ) Notice: Subject to any disclaimer, the term of this patent is extended or adjusted under 35 U.S.C. 154(b) by 42 days.

(21) Appl. No.: 10/955,766

(22) Filed: Sep. 30, 2004

(65) Prior Publication Data
US 2006/0065275 A1 Mar. 30, 2006

(51) Int. Cl.
*A61B 19/00* (2006.01)
(52) U.S. Cl. .................. 128/849; 128/852; 128/853; 128/854
(58) Field of Classification Search .............. 128/849, 128/850, 852, 853, 854
See application file for complete search history.

(56) References Cited

U.S. PATENT DOCUMENTS

| | | | | |
|---|---|---|---|---|
| 3,826,253 | A | * | 7/1974 | Larsh et al. ................. 128/854 |
| 4,316,456 | A | * | 2/1982 | Stoneback .................. 128/852 |
| 4,524,767 | A | * | 6/1985 | Glassman ................... 128/854 |
| 4,905,710 | A | | 3/1990 | Jones |
| 5,445,165 | A | | 8/1995 | Fenwick |
| 5,778,891 | A | | 7/1998 | McMahan |
| 5,941,907 | A | * | 8/1999 | Augustine ................... 607/104 |
| 6,102,936 | A | * | 8/2000 | Augustine et al. ............ 607/96 |
| 6,167,885 | B1 | * | 1/2001 | Hanssen ..................... 128/849 |
| 6,314,959 | B1 | | 11/2001 | Griesbach et al. |
| 6,382,212 | B1 | | 5/2002 | Borchard |
| 6,615,836 | B1 | | 9/2003 | Griesbach et al. |
| 6,679,267 | B1 | | 1/2004 | McNeirney et al. |
| 6,694,981 | B1 | | 2/2004 | Gingles et al. |
| 6,725,864 | B1 | | 4/2004 | Ewonce et al. |
| 6,814,079 | B1 | | 11/2004 | Heaton et al. |
| 6,874,505 | B1 | * | 4/2005 | Fenwick et al. ............. 128/849 |

OTHER PUBLICATIONS

Web Site for BAIR HUGGER(R) Temperature management - www.arizant.com/arizanthealthcare/faw.shtml.

* cited by examiner

*Primary Examiner*—Henry Bennett
*Assistant Examiner*—Camtu Nguyen
(74) *Attorney, Agent, or Firm*—McAfee & Taft

(57) ABSTRACT

A disposable sterile surgical drape with pre-attached disposable sterile instruments for use in a selected surgical procedure is provided. The disposable sterile surgical drape basically comprises a drape having a size for covering an operating table and a patient thereon and having an incision opening formed therein, a patient heat distributing pad pre-attached to the bottom side of the drape, an absorbent cloth surrounding the incision opening pre-attached to the bottom side of the drape, a cover for the incision opening in the drape pre-attached to the top side of the drape, and the surgical instruments and connecting tubes or wires required to accomplish the surgical procedure pre-attached to the drape.

28 Claims, 2 Drawing Sheets

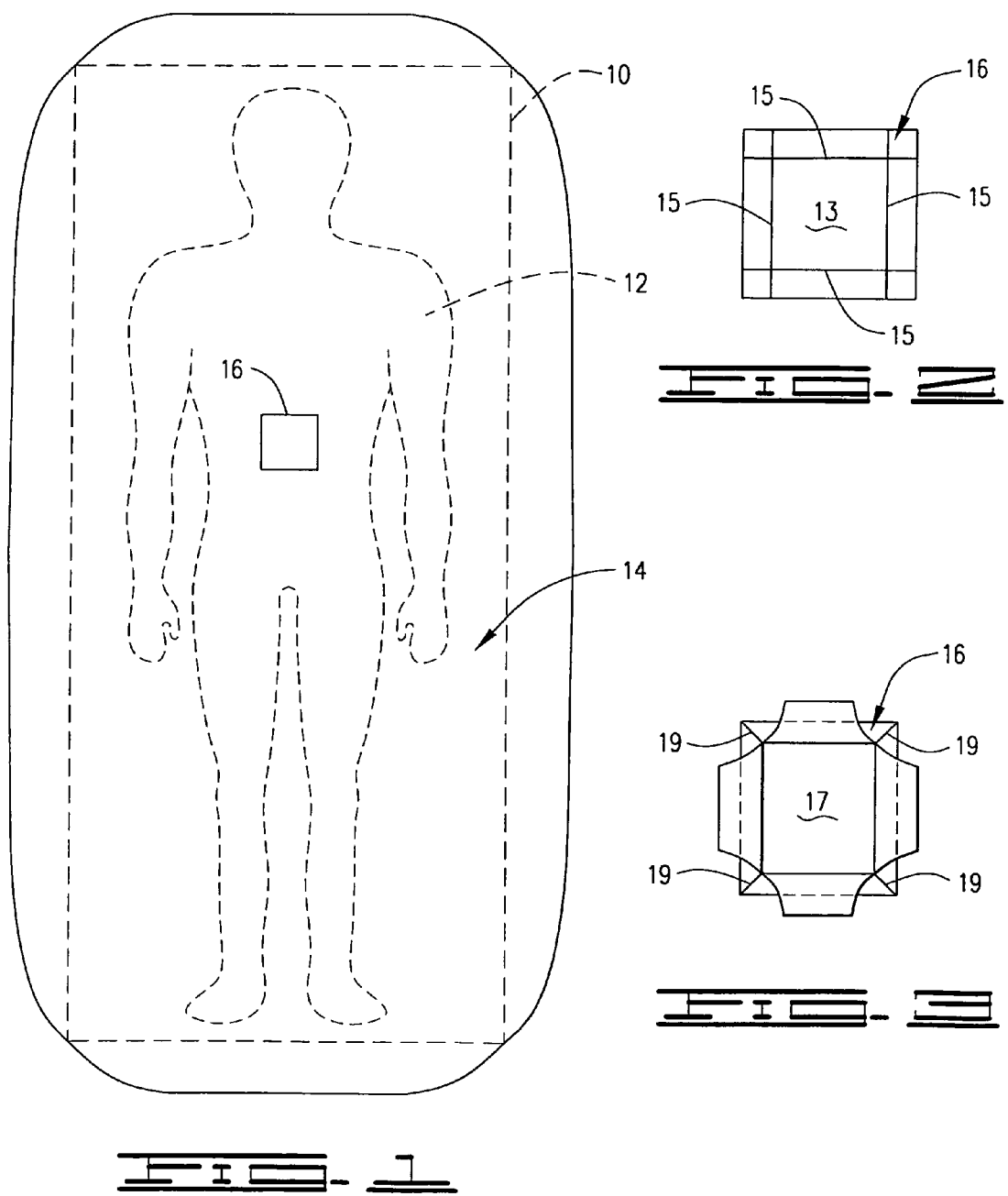

DISPOSABLE STERILE SURGICAL DRAPE AND ATTACHED INSTRUMENTS

BACKGROUND OF THE INVENTION

1. Field of the Invention

The present invention provides a disposable sterile drape with attached disposable sterile instruments for use in selected surgical procedures.

2. Description of the Prior Art

Surgical drapes are used during surgical procedures to create and maintain a sterile environment around the surgical site. The surgical drape creates and maintains a barrier that minimizes the passage of microorganisms between non-sterile and sterile areas. To be effective, the drape material must be resistant to blood, aqueous fluid and abrasion as well as being lint free. As a result, the surgical drape prevents blood and other bodily fluids from contaminating the sterile field, i.e., the incision and the patient's skin surrounding the incision.

Surgical drapes were originally formed of cotton or linen and were sterilized after each use. More recently, disposable drapes have been utilized formed of paper or fabric.

The surgical drapes commonly have an incision opening formed therein known in the medical field as a fenestration through which the surgical procedure is performed.

After a patient has been anesthetized in an operating room, the surgical team individually places the various components of the sterile drape and the instruments required on the patient. That is, a sterile heat distributing pad is placed on the patient to keep the patient warm followed by sterile absorbent towels which are placed on the patient around the surgical field. Thereafter, the sterile drape is placed on the patient so that the incision opening is positioned over the surgical field. A cover for the incision opening which is impregnated with iodine to kill bacteria, is transparent and includes an adhesive on one side is attached to the drape adjacent to the incision opening. The cover is positioned over the surgical field whereby it adheres to the drape and to the patient's skin within the surgical field. Finally, the various sterile surgical instruments and connecting tubes or wires required to accomplish the surgical procedure are placed on the sterile drape one at a time. This procedure of preparing the patient for surgery in the operating room after the patient has been anesthetized involves a lengthy period of time. Typically, the patient preparation time can take as long as forty-five minutes during which the patient is anesthetized.

Thus, there is a need for a patient preparation procedure utilizing sterile drape components and sterile surgical instruments that does not require the anesthetized patient and surgical team to be in the operating room for a long period of time before surgery can be performed. In addition, there is a need for a sterile drape having the various components pre-attached to the drape whereby there is little or no handling of the components by technicians or others not familiar with the components and as a result, the sterility of the drape and components is insured. Finally, there is a need for a sterile drape whereby the tubes and wires connected to the various sterile surgical instruments are attached to the drape between sterile layers of the drape whereby the tubes and wires are not contaminated from below or above the drape.

SUMMARY OF THE INVENTION

The present invention provides improved disposable sterile surgical drapes having disposable sterile instruments attached thereto for use in selected surgical procedures which meet the needs described above and overcome the deficiencies of the prior art.

A disposable sterile surgical drape of this invention having disposable sterile instruments attached thereto for use in a selected surgical procedure is comprised of the following components. A drape is provided having a size for covering an operating table and a patient thereon and having an enlargeable incision opening formed therein. An absorbent cloth surrounding the incision opening is pre-attached to the bottom side of the drape and a patient heat distributing pad is also pre-attached to the bottom side of the drape whereby it is positioned adjacent to the patient. A cover for the incision opening in the drape is pre-attached to the top side of the drape adjacent to the incision opening. The surgical instruments and connecting tubes or wires required to accomplish the surgical procedure are pre-attached to the top side of the drape.

The disposable sterile drape having disposable sterile instruments for use in a selected surgical procedure attached thereto is provided in a package which maintains the sterility of the drape and its attachments. The package is opened in the operating room and the disposable sterile surgical drape including attached disposable sterile instruments for a particular surgical -procedure is quickly and easily placed on the patient and the patient is ready for surgery in a very short period of time thereafter.

A disposable sterile drape with attached disposable sterile instruments for use in a lumbar surgical procedure comprises the following components. A drape is provided having a size for covering an operating table and a patient thereon and having an enlargeable incision opening formed therein. A patient heat distributing pad is pre-attached to the bottom side of the drape and an absorbent cloth surrounding the enlargeable incision opening is pre-attached to the bottom side of the drape. A sterile cover for the enlargeable incision opening in the drape is pre-attached to the top side of the drape adjacent to the incision opening. Finally, the surgical instruments and connecting tubes and wires required to perform the lumbar surgical procedure are attached to the top side of the drape.

The objects, features and advantages of the present invention will be readily apparent to those skilled in the art upon a reading of the description of preferred embodiments which follows when taken in conjunction with the accompanying drawings.

BRIEF DESCRIPTION OF THE DRAWINGS

FIG. 1 is a view of a patient on an operating room table with the surgical drape of the present invention placed thereon.

FIG. 2 is a view of a square enlargeable incision opening formed in the surgical drape of FIG. 1.

FIG. 3 is a view of a rectangular enlargeable incision opening formed in the surgical drape of FIG. 1.

DESCRIPTION OF PREFERRED EMBODIMENTS

Figure 4:
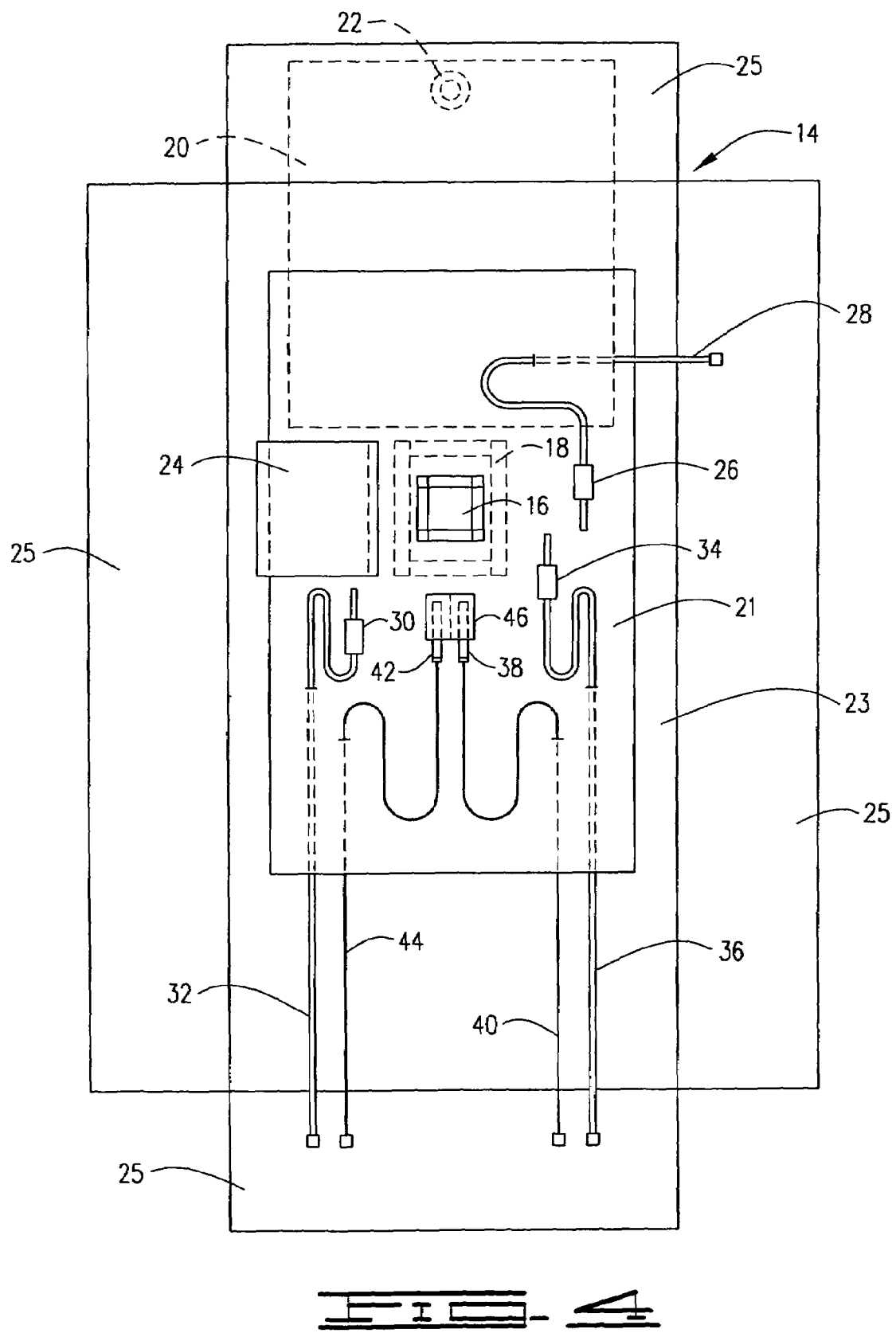
FIG. 4 is a top view of the surgical drape of this invention having the various components required for a lumbar surgical procedure pre-attached thereto.

A disposable sterile drape having pre-attached disposable sterile instruments of this invention for use in a selected surgical procedure is illustrated in the drawings. FIG. 1 is a top view of an operating table 10 having a patient 12 lying face down on the table 10. The table 10 and patient 12 are completely covered with a disposable sterile surgical drape 14 of this invention having a square enlargeable incision opening (also referred to as a fenestration) 16 therein. The enlargeable incision opening 16 in FIG. 1 is positioned for lumbar surgery from the patient's back.

The disposable sterile drape 14 is preferably formed of 2 attached together layers of paper, a top layer 21 which is plastic treated, and a bottom layer 23 having a skirt formed of four rectangular paper parts 25 attached thereto. The incision opening 16 is preferably square or rectangular. As illustrated in FIG. 2, the incision opening 16 can be a square opening 13 with slits 15 forming top, bottom and side flaps that can be folded back to form enlarged square or rectangular openings. As illustrated in FIG. 3, the incision opening 16 can be a rectangular opening 17 having 45° slits 19 extending from the corners thereof whereby the opening 17 can be enlarged by folding back the sides of the opening. Other incision openings shapes can also be utilized.

Referring now to FIG. 4, the disposable sterile drape 14 with pre-attached disposable sterile instruments and other components is illustrated. As described above, the disposable sterile drape 14 includes an enlargeable incision opening 16 formed therein.

A patient heat distributing pad 20 having heated air openings therein and a tube connection 22 for providing heated air thereto is attached to the bottom side of the drape 14. When the surgical drape 14 is utilized, the patient heat distributing pad 20 is connected to a source of heated air by way of a tube (not shown) connected to the tube connection 22. As will be understood by those skilled in the art, the heated air distributed by the heat distributing pad 20 keeps the patient warm during the surgical procedure. The heat distributing pad 20 includes an adhesive on the side adjacent to the patient whereby it adheres to the patient during the surgical procedure.

An absorbent cloth 18 preferably formed of several layers of toweling is also pre-attached to the bottom side of the drape 14 positioned around the enlargeable incision 16. The absorbent cloth 18 provides a barrier to absorb blood and other fluids during surgery.

A cover 24 for covering the incision opening in the drape is pre-attached to the top side of the drape along one side thereof adjacent to the incision opening 16. As mentioned above, the cover 24 is preferably impregnated with iodine to kill bacteria, is transparent and includes an adhesive on the top side so that it covers the incision opening 16 and sticks to the portion of the drape containing the incision opening and to the patient's exposed skin.

Depending upon the particular surgical procedure to be carried out, the disposable sterile instruments for the procedure are pre-attached to the drape. As mentioned above, the drape is sterile as are all the parts pre-attached to the drape including the instruments required to carry out the surgical procedure.

A specific procedure which utilizes the disposable sterile drape 14 illustrated in the drawing is a posterior lumbar surgery procedure. The sterile drape and instruments for the posterior lumbar surgery are illustrated in FIG. 4. More specifically, the surgical instruments and connecting tubes and wires required to perform the lumbar surgical procedure are pre-attached to the drape. That is, a portion of each tube and wire is attached between the top layer 21 and the bottom layer 23 of the drape so that the instruments are prevented from falling to the floor when not being used. The instrument 26 attached to the drape is a cell-saver suction instrument with a connecting tube 28. A first suction instrument 30 with a connecting tube 32 and a second suction instrument 34 with a connecting tube 36 are also attached to the drape 14. A bipolar cautery instrument 38 (less tip) having a connecting wire 40 and a monopolar cautery instrument 42 having a wire 44 are also attached to the drape 14. An instrument pocket 46 for the two cautery instruments is also attached to the top of the drape 14.

As will be understood by those skilled in the art, the tubes 28, 32 and 36 of the suction instruments are manually connected to additional tubes that connect to one or more suction machines. The wires 40 and 44 attached to the cautery instruments 38 and 42 are manually connected to additional wires that provide electricity thereto. When the surgical procedure has been accomplished, the tubes and wires are disconnected and the surgical drape 14 is removed from the patient. The surgical drape as well as the attached instruments, tubes and wires are then disposed of.

As will now be understood, disposable sterile surgical drapes of this invention with pre-attached instruments for performing various surgical procedures are provided in sealed packages. When a sterile drape is needed for a particular surgical procedure, the appropriate package is opened in the operating room and the sterile drape with pre-attached instruments is removed therefrom and quickly utilized. After being utilized, the package as well as the sterile drape and its attachments are disposed of.

A disposable sterile drape with attached disposable sterile instruments for use in a selected surgical procedure of this invention comprises: a drape having a size for covering an operating table and a patient thereon and having an incision opening formed therein; a patient heat distributing pad pre-attached to the bottom side of the drape; an absorbent cloth surrounding the incision opening pre-attached to the bottom side of the drape; a cover for the incision opening in the drape pre-attached to the top side of the drape adjacent to the incision opening; and the surgical instruments and connecting tubes or wires required to accomplish the surgical procedure pre-attached to the top side of the drape.

A disposable sterile drape with attached disposable sterile instruments for use in a lumbar surgical procedure of this invention comprises: a drape having a size for covering an operating table and a patient thereon and having an enlargeable incision opening formed therein; a patient heat distributing pad attached to the bottom side of the drape; an absorbent cloth surrounding the enlargeable incision opening pre-attached to the bottom side of the drape; a cover for the enlargeable incision opening in the drape pre-attached to the top side of the drape adjacent to the incision opening; and the surgical instruments and connecting tubes and wires required to perform the lumbar surgical procedure pre-attached to the top side of the drape.

As will be understood by those skilled in the art, numerous changes may be made to the disposable sterile surgical drape with pre-attached instruments of the present invention without departing from the spirit and scope of the invention as defined by the appended claims. For example, one or more incision openings of various shapes can be included in the disposable sterile surgical drape of this invention and a variety of the surgical procedures can be conducted using the disposable sterile surgical drape including, but not limited to, lumbar surgery, laparotomy surgery, thoracotomy surgery, median sternotomy surgery, extremity surgery, urologic surgery, gynecologic surgery or other surgery.

What is claimed is:

1. A disposable sterile surgical drape with pre-attached disposable sterile: instruments for use in a selected surgical procedure comprising:
    a drape having a size for covering an operating table and a patient thereon and having an incision opening formed therein;
    a patient heat distributing pad pre-attached to the bottom side of the drape;
    an absorbent cloth surrounding the incision opening pre-attached to the bottom side of the drape;
    a cover for the incision opening in the drape pre-attached to the top side of the drape adjacent to the incision opening; and
    the surgical instruments and connecting tubes or wires required to accomplish the surgical procedure pre-attached to the drape.

2. The disposable sterile surgical drape of claim 1 wherein the drape is formed of two layers of paper, the top layer being plastic treated.

3. The disposable sterile surgical drape of claim 1 wherein the drape includes a skirt formed of four rectangular paper parts.

4. The disposable sterile surgical drape of claim 1 wherein the incision opening is a square or rectangular opening.

5. The disposable sterile surgical drape of claim 1 wherein the incision opening is square and has top, bottom and side flaps that can be folded back to form an enlarged square or rectangular opening.

6. The disposable sterile surgical drape of claim 3 wherein the incision opening is rectangular and includes 45° slits extending from the corners thereof whereby the opening can be enlarged by folding back the sides of the opening.

7. The disposable sterile surgical drape of claim 1 wherein the heat distributing pad comprises heated air openings therein and a tube connection for providing heated air thereto.

8. The disposable sterile surgical drape of claim 1 wherein the heat distributing pad includes an adhesive on the side adjacent to the patient whereby it adheres to the patient.

9. The disposable sterile surgical drape of claim 1 wherein the absorbent cloth surrounding the enlargeable incision opening is formed of toweling.

10. The disposable sterile surgical drape of claim 1 wherein the cover for the incision opening is impregnated with iodine to kill bacteria, is transparent and includes an adhesive on the side adjacent to the patient whereby it adheres to the enlargeable incision opening and to the patient's exposed skin.

11. The disposable sterile drape of claim 1 which further comprises a package for containing the disposable sterile surgical drape and the attachments thereto and for maintaining the sterility thereof.

12. The disposable sterile surgical drape of claim 1 wherein the selected surgical procedure comprises lumbar surgery, laparotomy surgery, thoracotomy surgery, median sternotomy surgery, extremity surgery, urologic surgery, gynecologic surgery or other surgery.

13. A disposable sterile surgical drape with pre-attached disposable sterile instruments for use in a lumbar surgical procedure comprising:
    a drape having a size for covering an operating table and a patient thereon and having an enlargeable incision opening formed therein;
    a patient heat distributing pad pre-attached to the bottom side of the drape;
    an absorbent cloth surrounding the enlargeable incision opening pre- attached to the bottom side of the drape;
    a cover for the enlargeable incision opening in the drape pre-attached to the top side of the drape adjacent to the incision opening; and
    the surgical instruments and connecting tubes and wires required to perform the lumbar surgical procedure pre-attached to the drape.

14. The disposable sterile surgical drape of claim 13 wherein a cell-saver suction instrument with connecting tube is pre-attached to the drape.

15. The disposable sterile surgical drape of claim 13 wherein a first suction instrument with connecting tube is also pre-attached to the drape.

16. The disposable sterile surgical drape of claim 13 wherein a second suction instrument with connecting tube is also pre-attached to the drape.

17. The disposable sterile surgical drape of claim 13 wherein a bipolar cautery instrument with connecting wire is also pre-attached to the drape.

18. The disposable sterile surgical drape of claim 13 wherein a monopolar cautery instrument with connecting wire is also pre-attached to the drape.

19. The disposable sterile surgical drape of claim 13 wherein the surgical drape is formed of two layers of paper, the top layer being plastic treated.

20. The disposable sterile surgical drape of claim 13 wherein the drape includes a skirt formed of four rectangular paper parts.

21. The disposable sterile surgical drape of claim 13 wherein the incision opening is a square or rectangular opening.

22. The disposable sterile surgical drape of claim 13 wherein the incision opening is square and has top, bottom and side flaps that can be folded back to form an enlarged square or rectangular opening.

23. The disposable sterile surgical drape of claim 13 wherein the incision opening is rectangular and includes 45° slits extending from the corners thereof whereby the opening can be enlarged by folding back the sides of the opening.

24. The disposable sterile surgical drape of claim 13 wherein the heat distributing pad comprises heated air openings therein and a tube connection for providing heated air thereto.

25. The disposable sterile surgical drape of claim 13 wherein the heat distributing pad includes an adhesive on the side adjacent to the patient whereby it adheres to the patient.

26. The disposable sterile surgical drape of claim 13 wherein the absorbent cloth surrounding the enlargeable incision opening is formed of toweling.

27. The disposable sterile surgical drape of claim 13 wherein the cover for the incision opening is impregnated with iodine to kill bacteria, is transparent and includes an adhesive on the side adjacent to the patient whereby it adheres to the enlargeable incision opening and to the patient's exposed skin.

28. The disposable sterile surgical drape of claim 13 which further comprises a package for containing the disposable sterile surgical drape and the pre-attachments thereto and for maintaining the sterility thereof.

* * * * *

UNITED STATES PATENT AND TRADEMARK OFFICE
CERTIFICATE OF CORRECTION

| | | |
|---|---|---|
| PATENT NO. | : 7,096,870 B2 | Page 1 of 1 |
| APPLICATION NO. | : 10/995766 | |
| DATED | : August 29, 2006 | |
| INVENTOR(S) | : Lonnie Jay Lamprich and Bradley Keith Lamprich | |

It is certified that error appears in the above-identified patent and that said Letters Patent is hereby corrected as shown below:

Column 2, line 31, delete "-procedure" and substitute -- procedure -- therefor.

Column 5, line 6, delete the colon after "sterile."

Signed and Sealed this

Nineteenth Day of December, 2006

JON W. DUDAS
*Director of the United States Patent and Trademark Office*